(12) United States Patent
Jankowski

(10) Patent No.: US 7,846,149 B2
(45) Date of Patent: Dec. 7, 2010

(54) INSTRUMENT INTRODUCER

(75) Inventor: Bruce K. Jankowski, Meriden, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1122 days.

(21) Appl. No.: 10/510,942

(22) PCT Filed: Apr. 10, 2003

(86) PCT No.: PCT/US03/11244

§ 371 (c)(1),
(2), (4) Date: Oct. 8, 2004

(87) PCT Pub. No.: WO03/088854

PCT Pub. Date: Oct. 30, 2003

(65) Prior Publication Data

US 2005/0143756 A1    Jun. 30, 2005

Related U.S. Application Data

(60) Provisional application No. 60/373,032, filed on Apr. 15, 2002.

(51) Int. Cl.
*A61B 17/00* (2006.01)
(52) U.S. Cl. .......................... 606/1; 128/898
(58) Field of Classification Search .............. 606/1, 606/108; 128/898
See application file for complete search history.

(56) References Cited

U.S. PATENT DOCUMENTS

| | | | |
|---|---|---|---|
| 4,650,459 A * | 3/1987 | Sheldon | 604/15 |
| 5,228,851 A | 7/1993 | Burton | |
| 5,239,981 A | 8/1993 | Anapliotis | |
| 5,404,870 A | 4/1995 | Brinkerhoff et al. | |
| 5,634,937 A * | 6/1997 | Mollenauer et al. | 606/213 |
| 5,665,073 A | 9/1997 | Bulow et al. | |
| 5,738,220 A | 4/1998 | Geszler | |
| 5,752,970 A | 5/1998 | Yoon | |

(Continued)

FOREIGN PATENT DOCUMENTS

DE    100 11 042 A1    9/2001

(Continued)

OTHER PUBLICATIONS

PCT International Search Report for International Application No. PCT/US03/11244, Date Jul. 14, 2003 (5 pgs.).

(Continued)

*Primary Examiner*—John P Leubecker
*Assistant Examiner*—Victoria W Chen

(57) ABSTRACT

Instrument introducers are disclosed which facilitate the insertion of a surgical instrument into a cavity or a body of a patient. In one embodiment, the instrument introducer includes a hollow elongate cylindrical body including a distal end portion terminating in a distal edge and a proximal end portion, the cylindrical body defining a central longitudinal axis, and an elastomeric cap secured to the distal end portion of the cylindrical body, the cap including a distal end wall having an outer terminal edge and an annular side wall depending from the outer terminal edge thereof. The distal end wall includes an aperture formed therein, wherein a center of the aperture is coaxially aligned with the central longitudinal axis.

22 Claims, 4 Drawing Sheets

U.S. PATENT DOCUMENTS

| | | | |
|---|---|---|---|
| 5,792,074 A | | 8/1998 | Turkel et al. |
| 5,797,888 A | | 8/1998 | Yoon |
| 6,142,933 A | | 11/2000 | Longo et al. |
| 6,159,200 A | * | 12/2000 | Verdura et al. ............... 606/1 |
| 2002/0099258 A1 | * | 7/2002 | Staskin et al. ............... 606/1 |
| 2003/0120224 A1 | * | 6/2003 | Geiser et al. ............... 604/285 |

FOREIGN PATENT DOCUMENTS

| | | |
|---|---|---|
| EP | 01 58360 | 8/2001 |

OTHER PUBLICATIONS

International Search Report from International Application No. PCT/US03/11244 dated Jul. 22, 2003.

* cited by examiner

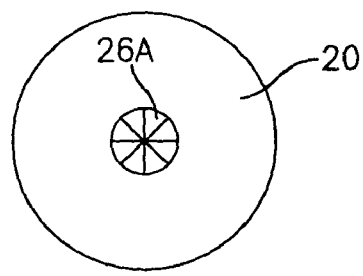
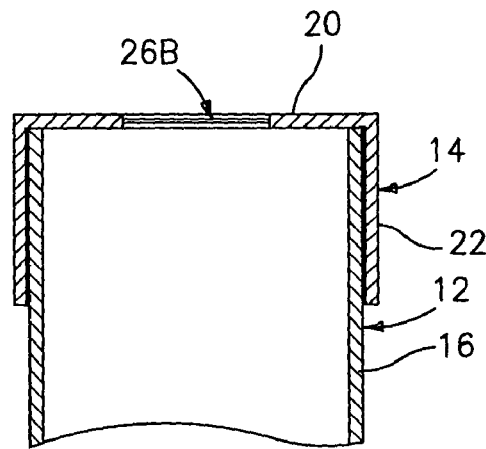
FIG. 2A
FIG. 2B
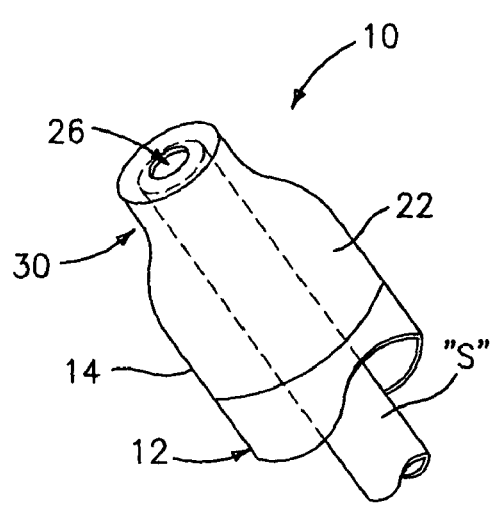
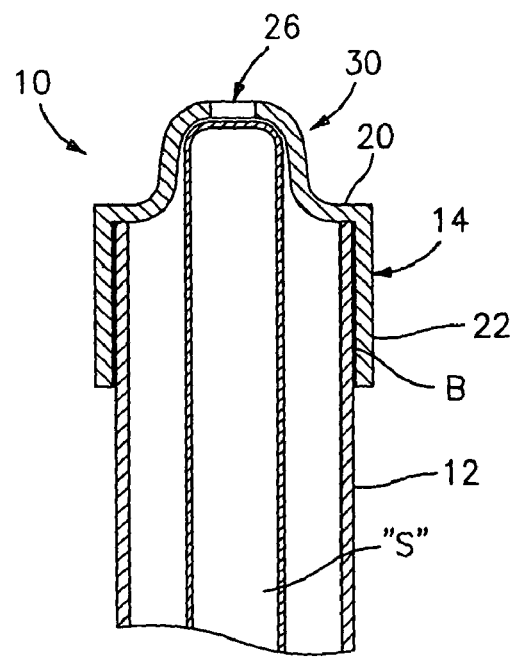
FIG. 3
FIG. 3A

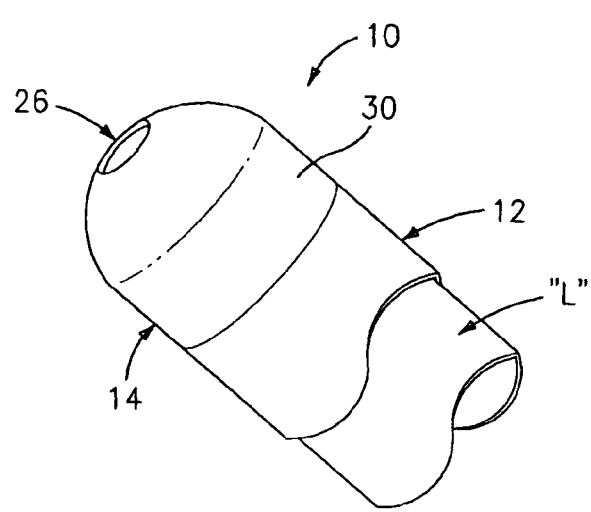
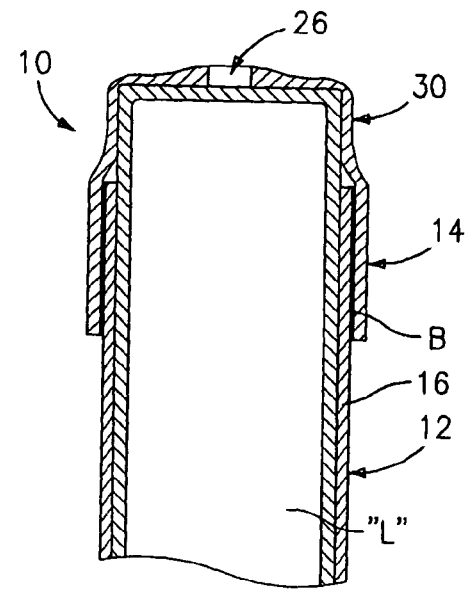
FIG. 4          FIG. 4A
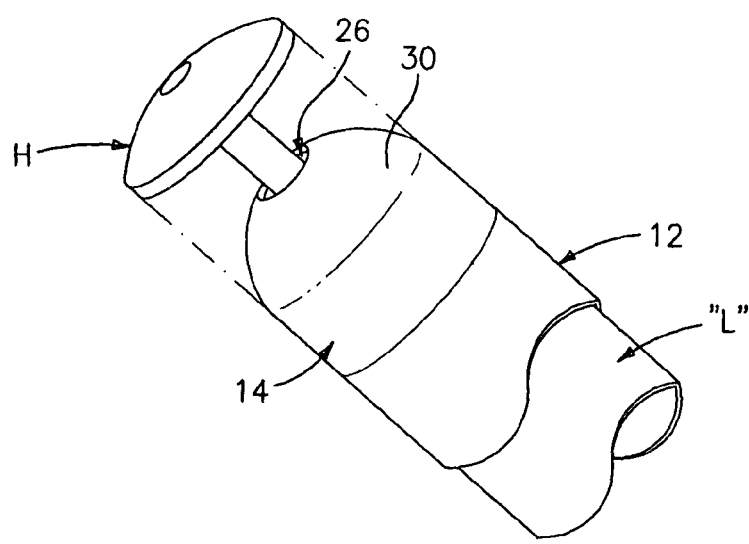
FIG. 5

INSTRUMENT INTRODUCER

CROSS-REFERENCE TO RELATED APPLICATION

The present application claims priority to U.S. Provisional Patent Application Ser. No. 60/373,032, filed Apr. 15, 2002, the entire contents of which are incorporated herein by reference.

BACKGROUND

1. Technical Field

The present disclosure relates to instrument introducers or protective sleeves and method of using the same, and more particularly, to novel protective sheaths configured to facilitate the introduction of surgical instruments into a cavity or a body opening of a patient.

2. Background of Related Art

Surgical instruments configured for remote use inside the body of a patient typically define a central longitudinal axis including a distal end portion and a proximal end portion. The distal end portion of the surgical instrument can include configurations which have either blunt or rounded faces and/or in certain instances include sharper subassemblies including electrosurgical or mechanical blades for cutting as well as fasteners for securing tissue portions. Typically, the distal end portions and, in particular, the distal end surfaces of these surgical instruments are such that irritation or trauma may be caused to the tissue surrounding the opening of the body through which the instrument is to be inserted. As a result of the mechanical complexity of these surgical instruments, the distal end portions of these instruments have been provided with a shell or cover that may partially or fully enclose the distal end portion of the surgical instrument.

For example, presently, various intra-anal surgical instruments, such as intraluminal anastomotic surgical staplers, require insertion into the colon or intestine through the anus. In certain embodiments, these surgical staplers have staple anvil portions removably mounted to a distal end thereof. Generally, the surgical stapler is inserted with the anvil portion attached, however, certain surgical procedures require that the surgical stapler is inserted into the colon or intestine through the anus with anvil portion removed.

Typically, in instances where the surgical stapler is to be inserted into the colon or intestine of the patient with the anvil portion mounted to a distal end thereof, the anvil portion is tapered inward toward the tip and formed to have an atraumatic end, thus facilitating the insertion of the distal end of the surgical instrument into the colon or intestine of the patient. However, in instances where the surgical stapler is to be inserted into the colon or intestine without the anvil portion mounted to a distal end thereof, the substantially squared or non-taped distal end of the surgical instrument may cause irritation and trauma to the surrounding tissue.

Thus, a need exists for a instrument introducer in the form of a sheath, which instrument introducer facilitates the passage of the surgical instrument into the body of the patient and that can be either adapted to be removably mounted on a distal end of the surgical instrument or be used as a separate device adapted to be positioned at least partially into the body of the patient (i.e., into the anus) and wherein the surgical instrument is subsequently positioned into the instrument introducer to facilitate insertion of the surgical instrument into the body of the patient.

SUMMARY

The present disclosure relates to instrument introducers configured to facilitate the introduction of surgical instruments into a cavity or a body opening of a patient. In one aspect of the present disclosure, the instrument introducer includes a tubular body portion defining a lumen therethrough, the tubular body portion having a proximal end and a distal end and a distal end portion secured to the distal end of the tubular body portion, the distal end portion including a distal end wall configured and adapted to facilitate passage of a surgical instrument therethrough.

It is contemplated that the distal end portion includes an annular side wall depending from an outer terminal edge thereof. Preferably, the distal end portion is made from an elastomeric material. The distal end wall of the distal end portion includes an aperture formed therein, wherein the aperture is preferably coaxially aligned with a central longitudinal axis of the tubular body portion.

In one embodiment the distal end portion is secured to the distal end of the tubular body portion such that the annular side wall at least partially overlaps the distal end of the tubular body portion. In another embodiment the distal end portion is secured to the distal end of the tubular body portion such that the annular side wall completely overlaps the distal end of the tubular body portion. In yet another embodiment a proximal terminal edge of the annular side wall of the distal end portion is secured to a distal terminal edge of the distal end of the tubular body. The distal end portion is secured to the distal end of the tubular body by fusing, overmolding, gluing and/or bonding.

The tubular body portion is preferably fabricated from polypropylene. In one embodiment, the instrument introducer includes a flange extending radially outward from the proximal end of the tubular body portion.

It is envisioned that the distal end wall of the distal end portion is provided with a region of weakened strength. The region of weakened strength includes score lines, perforations, webbing and/or reduced thickness. It is further envisioned that the distal end wall of the distal end portion is shaped to define a pocket.

In another aspect of the present disclosure the instrument introducer includes a hollow elongate cylindrical body including a distal end portion terminating in a distal edge and a proximal end portion, the cylindrical body defining a central longitudinal axis, and an elastomeric cap secured to the distal end portion of the cylindrical body, the cap including a distal end wall having an outer terminal edge and an annular side wall depending from the outer terminal edge thereof. The distal end wall includes an aperture formed therein, wherein a center of the aperture is coaxially aligned with the central longitudinal axis. It is envisioned that the cylindrical body is configured and adapted to receive a surgical instrument therethrough.

In one embodiment, the instrument introducer further includes a flange extending radially outward from a proximal terminal edge of the proximal end portion of the cylindrical body.

In one embodiment it is envisioned that the cap is secured to the distal end of the cylindrical body such that the distal end wall of the cap is spaced a distance from the distal terminal edge of the cylindrical body. In another embodiment it is envisioned that the cap is secured to the distal end of the cylindrical body such that a proximal terminal edge of the annular side wall is secured to the distal terminal edge of the cylindrical body.

It is contemplated that the distal end wall of the cap is shaped to define a pocket and wherein the aperture is formed in the pocket.

The present disclosure also discloses methods of introducing a surgical instrument into a cavity or a body opening of a patient. One method includes the step of providing an instrument introducer, wherein the instrument introducer includes a hollow tubular body having a distal end portion and a proximal end portion defining a lumen therebetween, and a resilient cap secured to the distal end of the tubular body, the cap having an aperture formed therein. The method further includes the steps of inserting the distal end of the instrument introducer into the cavity or body opening of the patient, inserting a surgical instrument into the lumen of the tubular body of the instrument introducer through a proximal end of the tubular body, and advancing the surgical instrument through the lumen of the tubular body of the instrument introducer until a distal end of the surgical instrument projects out through the aperture of the cap, wherein the cap creates a seal around the perimeter of the surgical instrument extending therefrom.

In another aspect of the method, a distal end of a surgical instrument is first inserted into a proximal end of the tubular body of the instrument introducer, the distal end of the surgical instrument, having the instrument introducer placed thereon, is then inserted into the cavity or body opening of the patient, the surgical instrument is then advanced through the instrument introducer until the distal end of the surgical instrument projects out through the aperture of the cap.

Accordingly, it is an object of the present disclosure to provide a surgical instrument introducer which facilitates the insertion of a distal end of the surgical instrument into a cavity or a body opening of a patient.

It a further object of the present disclosure to provide an instrument introducer which reduces the potential for irritation and/or trauma as a result of the insertion of the surgical instrument into the cavity or body opening of the patient if the surgical instrument were to be inserted into the cavity or body opening of the patient without the instrument introducer operatively coupled thereto.

The presently disclosed instrument introducer, together with attendant advantages, will be more clearly illustrated below by the description of the drawings and the detailed description of the preferred embodiments.

Other objects and features of the present disclosure will become apparent from consideration of the following description taken in conjunction with the accompanying drawings.

BRIEF DESCRIPTION OF THE DRAWINGS

By way of example only, preferred embodiments of the disclosure will be described with reference to the accompanying drawings, in which:

FIG. 2A is an end view of an alternative embodiment of a distal end wall of the distal end portion of an instrument introducer in accordance with the present disclosure;

FIG. 2B is a cross-sectional side elevational view of the distal end portion of an instrument introducer depicting another alternative embodiment of a distal end wall in accordance with the present disclosure;

FIG. 3 is a perspective view, with portions broken away, of an alternative embodiment of a distal end portion of the instrument introducer depicted in FIG. 1, with a distal end portion of a relatively smaller diameter surgical instrument inserted into the distal end thereof;

FIG. 3A is a cross-sectional side elevational view, taken along the longitudinal axis, of the instrument introducer depicted in FIG. 3, depicting the distal end of the relatively smaller diameter surgical instrument inserted therein;

FIG. 4 is a perspective view, with portions broken away, of the instrument introducer depicted in FIG. 1, with a distal end portion of a relatively larger diameter surgical instrument inserted into the distal end thereof;

FIG. 4A is a cross-sectional side elevational view, taken along the longitudinal axis, of the introducer depicted in FIG. 4, depicting the distal end of the relatively larger diameter surgical instrument inserted therein;

FIG. 5 is a perspective view of an instrument introducer as depicted in FIG. 1, illustrating the passage of an anvil assembly of a surgical instrument through a passage formed in a distal end surface thereof;

DETAILED DESCRIPTION OF PREFERRED EMBODIMENTS

Figures 1, 1A:
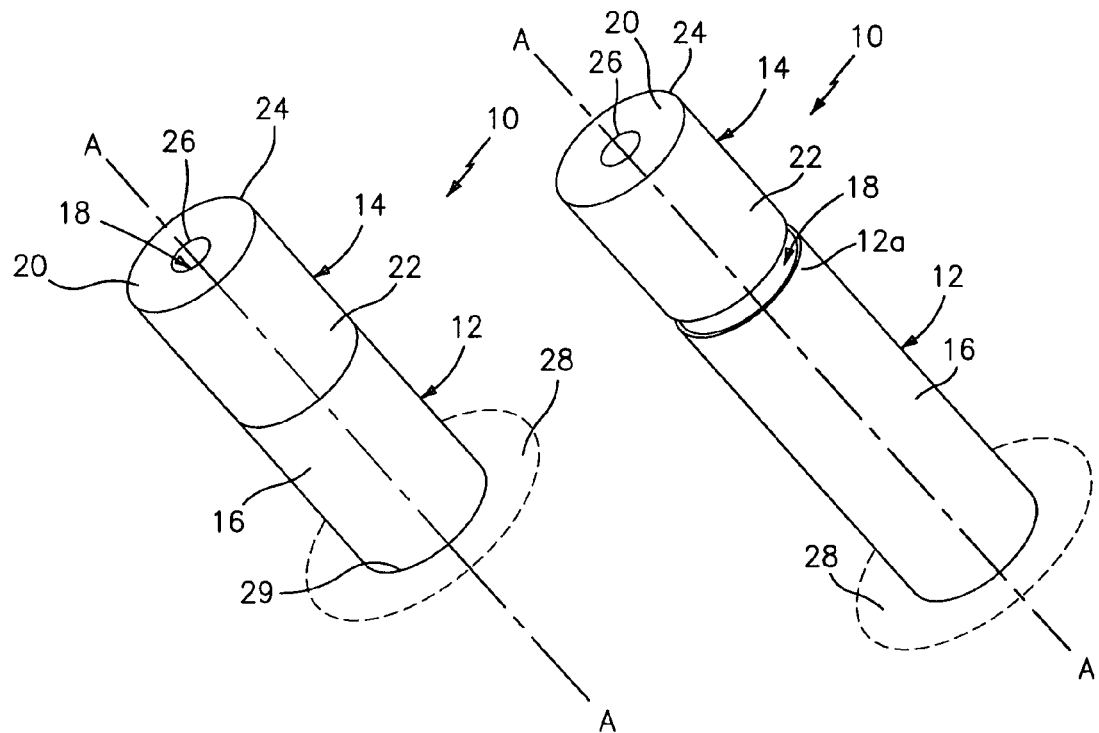
FIG. 1 is a top perspective view of an instrument introducer in accordance with an embodiment of the present disclosure having a flange adjacent a proximal end.
FIG. 1A is an exploded top perspective view of the instrument introducer depicted in FIG. 1.

While the device according to the present disclosure is especially suitable for introducing a distal end portion of a surgical instrument into body cavities, such as, for example, anal orifices, the external urethral opening or the mouth of a patient, for performing, for example, hemorrhoidal or end-to-end anastomotic applications, it is envisioned that the device according to the present disclosure can be used in connection with other surgical instruments for performing any number of other endoscopic or laparoscopic surgical procedures. For example, it is believed that the device disclosed herein may find use in other procedures in which blunt ended surgical instruments are introduced into the bodies of patients.

In the drawings and in the description which follows, the term "proximal", as is traditional will refer to the end of the surgical device or instrument of the present disclosure which is closest to the operator, while the term "distal" will refer to the end of the device or instrument which is furthest from the operator.

Referring now in specific detail to the drawings, in which like reference numerals identify similar or identical elements, FIGS. 1, 1A, 1B and 1C illustrate a surgical instrument introducer generally designated with the reference numeral 10. Surgical instrument introducer 10 is in the form of a sheath, drape, sock, sleeve, covering, casing, condom, etc. Accordingly, as used herein, instrument introducer 10 can embody any one of these terms.

As will be further described below, instrument introducer 10 is configured and adapted to be either removably mounted on a distal end portion of a surgical instrument (e.g., anastomotic stapler) prior to insertion of the surgical instrument into an orifice of the body or for initial placement into the orifice of the body and for subsequent insertion of the distal end portion of the surgical instrument therein. Preferably, instrument introducer 10 has a shape which facilitates its entry into the orifice of the body and which is also compatible with the distal end portion of the surgical instrument. It is contemplated that instrument introducer 10 functions as a protective sheath or sleeve to cap the distal end of and to facilitate the entry of the distal end portion of the surgical instrument into the orifice of the body. In addition, instrument introducer 10 can act as an insulative barrier and/or an isolating barrier between the surgical instrument and the body of the patient.

In a preferred embodiment, introducer 10 has two principle sections, namely, a hollow tubular section 12 and a distal end portion 14 affixed adjacent to a distal edge 12*a* (see FIG. 1A) of tubular section 12. It is contemplated that instrument introducer 10 may be constructed from a tubular section 12 and a distal end portion 14 made from different materials which are in turn joined together, or introducer 10 may be monolithically formed in which case tubular section 12 and distal end portion 14 are made from a single material specifically selected depending upon its desired application.

Hollow tubular section 12 includes an annular wall 16 defining a lumen 18 therethrough, which lumen 18 defines a central longitudinal axis "A". Preferably, annular wall 16 has an inner diameter sized to receive a distal end portion of the surgical instrument. It is envisioned that tubular section 12 can vary in length depending on the surgical instrument that is going to be inserted into the orifice of the body through lumen 18 and depending on the particular surgical application in which instrument introducer 10 is going to be used. Preferably, tubular section 12 will vary in length from about two inches to about eight inches.

Tubular section 12 is preferably fabricated from a suitable moldable plastic material with sufficient pliability to provide for controlled deflection and sufficient stiffness to retain shape during insertion and use. Tubular section 12 is preferably fabricated from polypropylene or like acceptable medical grade material capable of sterilization.

In a preferred embodiment, distal end portion 14 is in the form of a cap having a preferably circular distal end wall 20 and an annular side wall 22 depending substantially orthogonally from an outer terminal edge 24 of end wall 20. End wall 20 bounds a circular through-hole 26 formed therein, wherein a central axis of through-hole 26 is substantially co-axial with central longitudinal axis "A" of lumen 18. While the central axis of through-hole 26 has been described as being co-axial with longitudinal axis "A", it is envisioned that through-hole 26 need not be concentric with lumen 18 or that end wall 20 can define additional holes having varying alignments and directional orientations for the passage of portions of a surgical instrument therethrough.

Distal end portion 14 of instrument introducer 10, and preferably at least distal end wall 20 of distal end portion 14, is fabricated from a flexible/pliable/stretchable material, preferably a thermoformable material, more preferably, an extrudable or injection moldable material, and most preferably an elastomer or elastomeric material. Distal end portion 14 is configured and adapted for receiving the distal end of the surgical instrument therein, and for deforming and yielding about the distal end of the surgical instrument during the advancement of the distal end of the surgical instrument through lumen 18 of tubular section 12 and against an inner surface of distal end wall 20 of distal end portion 14.

In an alternative embodiment, it is contemplated that through-hole 26 can be partially or fully closed, or distal end wall 20 can be weakened by score lines 26A (see FIG. 2A), thinned (see FIG. 2B), provided with perforations or webbed portions (not shown) which define the bounds of through-hole 26. In still a further embodiment, through-hole 26 can be a slit formed in end wall 20 of distal end portion 14. In this embodiment, through-hole 26 of distal end portion 14 is subsequently opened or created by the operator of the surgical instrument and/or instrument introducer 10 or by the application of an axial force to the inner surface of distal end wall 20 upon advancement of the distal end of the surgical instrument through lumen 18 of instrument introducer 10 and against the weakened distal end wall 20.

Figures 1B, 1C:
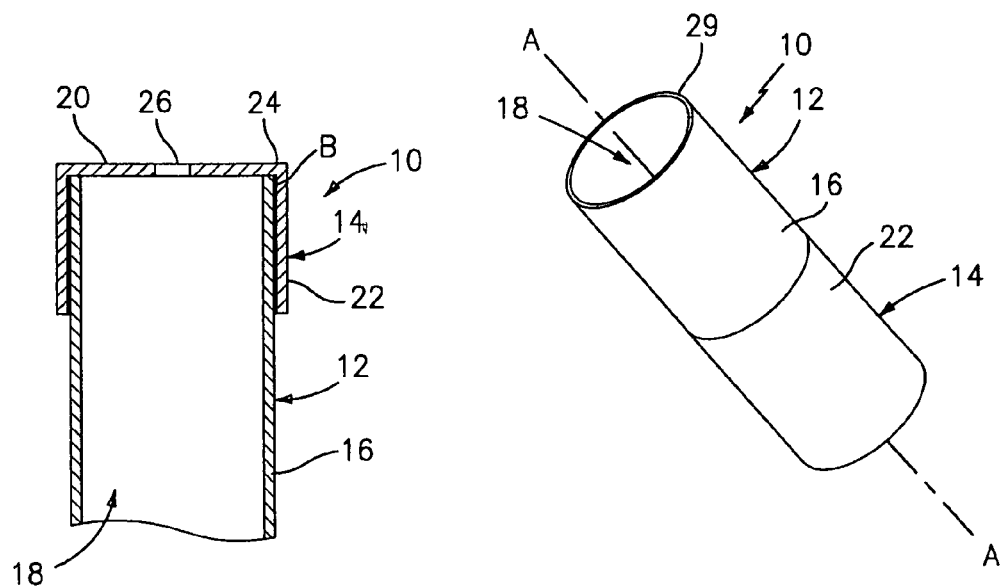
FIG. 1B is a cross-sectional side view, taken along the longitudinal axis, of a distal end of the instrument introducer depicted in FIG. 1.
FIG. 1C is a bottom perspective view of the instrument introducer depicted in FIG. 1, with the flange removed.

Turning back to FIGS. 1-1C and, in particular to FIG. 1B, preferably, annular side wall 22 of distal end portion 14 has an inner diameter which is substantially equal to the outer diameter of tubular section 12. As such, distal end portion 14 is snuggly fitted over the distal end portion of tubular section 12. Accordingly, distal end portion 14 is restricted or prevented from sliding off of distal edge 12*a* of tubular section 12, thereby reducing the susceptibility of distal end portion 14 from separating from tubular section 12.

As seen in FIG. 1B, distal end portion 14 is preferably secured at "B" about the distal end of tubular section 12. It is contemplated that distal end portion 14 is secured about the distal end of tubular section 12 by fusion, a two shot, overmold, gluing, or other bonding processes known by those skilled in the art. Further, in the present embodiment, the entire length of annular side wall 22 of distal end portion 14 is preferably in contact with and subsequently bonded to the distal end of tubular section 12.

It is envisioned that when instrument introducer 10 is adapted to be initially coupled to or to be removably coupled on the distal end portion of the surgical instrument, instrument introducer 10 can be coupled thereto using, for example, mechanical lugs, directly overmolding the material, suitable adhesives, mechanical friction enhancing surface finishes, or heat shrinking.

In another preferred embodiment, as seen in FIGS. 1 and 1A, tubular section 12 includes a structure having one or more radially outwardly extending portions such as tabs or more preferably such as a continuous flange 28 (represented as dashed lines in FIGS. 1 and 1A) integral with or connected to a proximal edge 29 of tubular section 12. In one aspect of the disclosure, flange 28 functions to limit the depth of entry of instrument introducer 10 into the body of the patient. Flange 28 can advantageously provide a surface suitable for the positioning of adhesives or tapes, e.g., such as those sold under the trademark Steri-strip, to fix or secure instrument introducer 10 and potentially the surgical instrument relative to the patient and to limit the depth of penetration of instrument introducer 10 and/or the distal end of the surgical instrument into the body of the patient. While it is envisioned that flange 28 is to be used when instrument introducer 10 is employed as a stand alone device that is unconnected to a surgical instrument, it is envisioned that an instrument introducer 10 having a flange 28 can also be employed when instrument introducer 10 is connected to the surgical instrument prior to insertion of instrument introducer 10 into the cavity or body opening of the patient.

While distal end portion 14 of instrument introducer 10 is preferably a flexible/pliable/stretchable material adapted to accommodate the distal end portion of a surgical instrument, alternative embodiments are envisioned where distal end portion 14 utilizes predisposed or formed folds or combinations of folds which flex and/or stretch and have a shape suitable for penetration and passage of the tip, head, assembly, subassembly or end effector of the surgical instrument. In a further alternative embodiment, distal end portion 14 can be fabricated from a radially expandable mesh such that distal end portion 14 is expandable to accommodate the distal end portion of the surgical instrument.

While two different materials have been described herein with reference to respective tubular section 12 and distal end portion 14, it is envisioned that a single elastomer or combinations of elastomers and flexible/stretchable materials of different durometers, having suitable characteristics, may be used to fabricate instrument introducer 10. For example, distal end wall 20 can have a durometer that renders it more flexible than annular side wall 22 thereby permitting the distal end portion of a surgical instrument to more easily pass through through-hole 26 of distal end portion 14.

Turning now to FIGS. 3 and 3A, an alternative embodiment of an instrument introducer 10 is illustrated. As shown in FIGS. 3 and 3A, instrument introducer 10 includes a distal end portion 14 in which the distal end wall thereof defines a pocket 30. Pocket 30 extends distally or proximally from distal end wall 20 and is defined by having a diameter which is less than the diameter of annular side wall 22. In addition, pocket 30 is provided with through-hole 26 centrally formed therein. Preferably, the diameter of pocket 30 substantially corresponds to a diameter of a distal end of a surgical instrument "S" which has a relatively smaller diameter than the inner diameter of annular wall 16 of tubular section 12. Accordingly, when relatively smaller diameter surgical instrument "S" is received within instrument introducer 10, the distal end of smaller diameter surgical instrument "S" is snuggly received within pocket 30. As smaller diameter surgical instrument "S" is advanced distally through instrument introducer 10, pocket 30 stretches/flexes distally and through-hole 26 stretches/flexes radially outward to a diameter sufficient to accommodate the passage of smaller diameter surgical instrument "S" therethrough.

Turning now to FIGS. 4 and 4A, a relatively larger diameter surgical instrument "L", having an outer diameter slightly smaller than the inner diameter of annular wall 16 of tubular section 12, is shown inserted into instrument introducer 10. As larger diameter surgical instrument "L" is advanced distally through instrument introducer 10, pocket 30 stretches/flexes to conform to the shape of the distal end of the larger diameter surgical instrument "L". As larger diameter surgical instrument "L" is further advanced through instrument introducer 10, through-hole 26 stretches/flexes radially outward to a diameter sufficient to accommodate the passage of the larger diameter surgical instrument "L" therethrough.

As seen in FIG. 5, distal end portion 14, including through-hole 26, can have sufficient elasticity to accommodate the passage of a head "H" of either smaller or larger diameter surgical instrument "S" or "L" through through-hole 26, and is suitably biased in each instance to return to the first unstretched state after passage of head "H" therethrough. Instrument introducer 10 is configured to stretch/flex in order to accommodate the passage of head "H" of smaller or larger surgical instrument "S" or "L" therethrough as head "H" is passes proximally and distally across through-hole 26.

Figure 6:
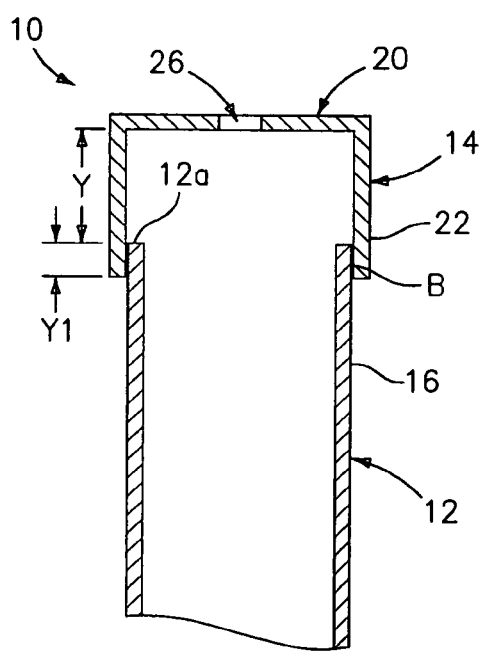
FIG. 6 is a cross-sectional side view, taken along a longitudinal axis, of an instrument introducer in accordance with an alternative embodiment of the present disclosure.
Figure 7:
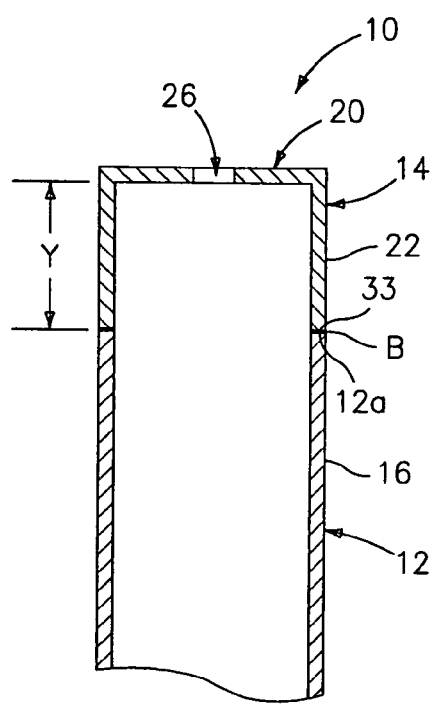
FIG. 7 is a cross-sectional side view, taken along a longitudinal axis, of an instrument introducer in accordance with another alternative embodiment of the present disclosure.

Turning now to FIGS. 6 and 7, alternative embodiments of instrument introducer 10 are disclosed. As seen in FIGS. 6 and 7, it is envisioned that distal end wall 20 of distal end portion 14 is spaced a distance "Y" from a distal edge 12a of tubular section 12. In the embodiment shown in FIG. 6, the internal surface of annular side wall 22 of distal end portion 14 is in contact with the outer surface of a distal end of annular wall 16 of tubular section 12 such that distal end wall 20 is spaced a distance "Y" from distal edge 12a of tubular section 12. In addition, annular side wall 22 of distal end portion 14 overlaps the distal end of annular wall 16 of tubular section 12 by an amount "Y1". As described above, preferably, the inner surface of annular wall 22 of distal end portion 14 is fused, bonded, etc, at "B", to the outer surface of annular wall 16 of tubular section 12.

In the embodiment shown in FIG. 7, it is envisioned that a proximal edge 33 of annular side wall 22 of distal end portion 14 is fused, bonded, etc., at "B", to distal edge 12a of tubular section 12. In this manner, the entire length of annular wall 22 of distal end portion 14 extends from tubular section 12.

Operation of instrument introducer 10 will now be described with reference to FIGS. 1-5. In a preferred method of use, instrument introducer 10 is initially positioned on a distal end portion of a surgical instrument. As the distal end portion of the surgical instrument, with instrument introducer 10 positioned thereon, is inserted and/or introduced into a cavity or body opening of a patient (e.g., the anus), the flexible/stretchable distal end wall 20 of distal end portion 14 of instrument introducer 10 is flexed/stretched in an axial direction as a result of the side walls of the cavity or body opening of the patient creating a resistance to the advancement of instrument introducer 10 and the continued distal advancement of the surgical instrument through lumen 18 of instrument introducer 10. As the surgical instrument is further advanced distally, the distal end portion of the surgical instrument at least partially deforms and/or stretches distal end portion 14 of instrument introducer 10 and deforms and/or stretches through-hole 26, radially enlarging it, to a diameter sufficient to accommodate the passage of head "H" of the surgical instrument through instrument introducer 10 and, if need be, to accommodate the passage of the distal end portion of the surgical instrument (not shown).

In an alternative method of use, instrument introducer 10 is initially placed within the cavity or body opening of the patient such that distal end portion 14 of instrument introducer 10 is retained therein. With instrument introducer 10 in place, the distal end of a surgical instrument is inserted within lumen 18 of instrument introducer 10 and advanced until the distal end of the surgical instrument contacts the inner surface of distal end wall 20 of distal end portion 14 of instrument introducer 10. Similar to the method described above, as the surgical instrument is further advanced distally within instrument introducer 10, the distal end portion of the surgical instrument begins to partially deform and/or stretch distal end portion 14 of instrument introducer 10 and to deform and/or stretch hole 26 and radially enlarge it to a diameter sufficient to accommodate the passage of head "H" of the surgical instrument through instrument introducer 10 and, if need be, to accommodate the passage of the distal end portion of the surgical instrument (not shown).

In either method, it is understood by those skilled in the art that flange 28 will limit the depth of penetration of instrument introducer 10 into the cavity or the body opening of the patient. Additionally, in either method, it is contemplated that a lubricant be applied to the outer surface of instrument introducer 10 in order to facilitate insertion of instrument introducer 10 into the cavity or body opening of the patient and optionally to the inner surface of instrument introducer 10 and/or the outer surface of the surgical instrument in order to facilitate the insertion of the surgical instrument into instrument introducer 10.

Although the illustrative embodiments of the present disclosure have been described herein, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A surgical instrument and instrument introducer assembly for facilitating the insertion of the surgical instrument into a cavity or a body opening of a patient, comprising:
   a surgical instrument for performing a surgical procedure; and
   an instrument introducer assembly including:
      a tubular body portion defining a lumen therethrough, the tubular body portion having a proximal end and a distal end; and
      a distal end portion secured to the distal end of the tubular body portion, the distal end portion defining a pocket having an annular wall with an axial length such that the annular wall of the pocket is substantially in contact with an outer surface of the surgical instrument along substantially the length of the pocket and including a substantially planar distal end wall configured and adapted to stretch and conform to a shape of the outer surface of the surgical instrument to facilitate passage of the surgical instrument in a sealing relation to the surgical instrument;
   wherein the surgical instrument stretches the distal end portion of the instrument introducer as it is advanced therethrough.

2. The instrument introducer according to claim 1, wherein the distal end portion includes an annular side wall depending from an outer terminal edge thereof.

3. The instrument introducer according to claim 2, wherein the distal end portion is made from an elastomeric material.

4. The instrument introducer according to claim 3, wherein the distal end wall of the distal end portion is provided with a region of weakened strength.

5. The instrument introducer according to claim 4, wherein the region of weakened strength includes at least one of score lines, perforations, webbing and reduced thickness.

6. The instrument introducer according to claim 2, wherein the distal end wall of the distal end portion includes an aperture formed therein.

7. The instrument introducer according claim 6, wherein the aperture is coaxially aligned with a central longitudinal axis of the tubular body portion.

8. The instrument introducer according to claim 6, wherein the distal end portion is secured to the distal end of the tubular body portion such that the annular side wall at least partially overlaps the distal end of the tubular body portion.

9. The instrument introducer according to claim 8, wherein the distal end portion is secured to the distal end of the tubular body portion such that the annular side wall completely overlaps the distal end of the tubular body portion.

10. The instrument introducer according to claim 9, wherein the distal end portion is secured to the distal end of the tubular body by at least one of fusing, overmolding, gluing and bonding.

11. The instrument introducer according to claim 6, wherein a proximal terminal edge of the annular side wall of the distal end portion is secured to a distal terminal edge of the distal end of the tubular body.

12. The instrument introducer according to claim 6, wherein the tubular body portion is fabricated from polypropylene.

13. The instrument introducer according to claim 6, further including a flange extending radially outward from the proximal end of the tubular body portion.

14. The instrument introducer according to claim 6, wherein the distal end portion has a frustoconical profile including a concave annular side wall.

15. A surgical instrument and instrument introducer assembly for facilitating the insertion of the surgical instrument into a cavity or a body of a patient, comprising:
   a surgical instrument for performing a surgical procedure; and
   an instrument introducer assembly including:
      a hollow elongate cylindrical body including a distal end portion terminating in a distal edge and a proximal end portion, the cylindrical body defining a central longitudinal axis; and
      an elastomeric cap secured to the distal end portion of the cylindrical body, the cap defining a pocket having an annular wall with an axial length such that the annular wall of the pocket is substantially in contact with an outer surface of the surgical instrument along substantially the length of the pocket and including a substantially planar distal end wall having an outer terminal edge and an annular side wall depending from the outer terminal edge thereof, the distal end wall including an aperture formed in the pocket configured and adapted to stretch and conform to a shape of the outer surface of the surgical instrument to facilitate passage of the surgical instrument therethrough in a sealing relation to the surgical instrument, wherein a center of the aperture is coaxially aligned with the central longitudinal axis;
   wherein the surgical instrument stretches the aperture of the distal end wall of the instrument introducer as it is advanced therethrough.

16. The instrument introducer according to claim 15, wherein the cylindrical body is configured and adapted to receive a surgical instrument therethrough.

17. The instrument introducer according to claim 15, further including a flange extending radially outward from a proximal terminal edge of the proximal end portion of the cylindrical body.

18. The instrument introducer according to claim 15, wherein the cap is secured to the distal end of the cylindrical body such that the distal end wall of the cap is spaced a distance from the distal terminal edge of the cylindrical body.

19. The instrument introducer according to claim 15, wherein the cap is secured to the distal end of the cylindrical body such that a proximal terminal edge of the annular side wall is secured to the distal terminal edge of the cylindrical body.

20. The instrument introducer according to claim 15, wherein the distal end portion has a frustoconical profile including a concave annular side wall.

21. A method of introducing a surgical instrument into a cavity or a body opening of a patient, comprising the steps of:
   providing a surgical instrument for performing a surgical procedure;
   providing an instrument introducer assembly, wherein the instrument introducer includes a hollow tubular body having a distal end portion and a proximal end portion defining a lumen therebetween, and a resilient cap secured to the distal end of the tubular body, the cap defining a pocket having an annular wall with an axial length such that the annular wall of the pocket is substantially in contact with an outer surface of the surgical instrument along substantially the length of the pocket and including a substantially planar distal end wall having an aperture formed therein;

inserting the distal end of the instrument introducer into the cavity or body opening of the patient;

inserting the surgical instrument into the lumen of the tubular body of the instrument introducer through a proximal end of the tubular body; and advancing the surgical instrument through the lumen of the tubular body of the instrument introducer thereby stretching the instrument introducer such that the aperture of the distal end wall stretches and conforms to a shape of the outer surface of the surgical instrument until a distal end of the surgical instrument projects out through the aperture of the cap, wherein the cap creates a seal around the perimeter of the surgical instrument extending therefrom.

22. A method of introducing a surgical instrument into a cavity or a body opening of a patient, comprising the steps of:

providing a surgical instrument for performing a surgical procedure;

providing an instrument introducer assembly, wherein the instrument introducer includes a hollow tubular body having a distal end portion and a proximal end portion defining a lumen therebetween, and a resilient cap secured to the distal end of the tubular body, the cap defining a pocket having an annular wall with an axial length such that the annular wall of the pocket is substantially in contact with an outer surface of the surgical instrument along substantially the length of the pocket and including a substantially planar distal end wall having an aperture formed therein;

inserting a distal end of the surgical instrument into a proximal end of the tubular body of the instrument introducer;

inserting the distal end of the surgical instrument, having the instrument introducer placed thereon, into the cavity or body opening of the patient; and advancing the surgical instrument through the instrument introducer thereby stretching the instrument introducer such that the aperture of the distal end wall stretches and conforms to a shape of the outer surface of the surgical instrument until the distal end of the surgical instrument projects out through the aperture of the cap, wherein the cap creates a seal around the perimeter of the surgical instrument extending therefrom.

* * * * *